United States Patent [19]

Cohen

[11] Patent Number: 5,330,521
[45] Date of Patent: Jul. 19, 1994

[54] LOW RESISTANCE IMPLANTABLE ELECTRICAL LEADS

[76] Inventor: Donald M. Cohen, 17512 Luther Ave., Irvine, Calif. 92714

[21] Appl. No.: 905,771

[22] Filed: Jun. 29, 1992

[51] Int. Cl.$^5$ .......................................... A61N 1/05
[52] U.S. Cl. ................................................. 607/122
[58] Field of Search ................... 128/419 P, 784, 785, 128/786

[56] References Cited

U.S. PATENT DOCUMENTS

| | | | |
|---|---|---|---|
| 3,974,834 | 8/1976 | Kane | 128/418 |
| 4,402,329 | 9/1983 | Williams | 128/785 |
| 4,643,201 | 2/1987 | Stokes | 128/786 |
| 4,649,938 | 3/1987 | McArthur | 128/785 |
| 4,774,952 | 10/1988 | Smits | 128/419 |
| 4,815,469 | 3/1989 | Cohen et al. | 128/634 |
| 4,884,567 | 12/1989 | Elliott et al. | 128/303 |
| 4,946,457 | 8/1990 | Elliott | 606/1 |
| 4,991,603 | 2/1991 | Cohen et al. | 128/786 |
| 4,998,975 | 3/1991 | Cohen et al. | 128/419 |
| 5,097,843 | 3/1992 | Soukup et al. | 128/784 |

OTHER PUBLICATIONS

Stokes, et al., "A New Efficient NanoTip Lead", *PACE*, vol. 13, pp. 1901–1905 (Dec. 1990).
Mond, et al., "The Electrode-Tissue Interface: The Revolutionary Role of Steroid Elution", *PACE*, vol. 15, pp. 95–107 (Jan. 1992).
Schladach, et al., "Sputter-Deposited TiN Electrode Coatings for Superior Sensing and Pacing Performance", *PACE*, vol. 13, pp. 1891–1751 (Dec. 1990).
Stokes, et al., "The Mythology of Threshold Variations as a Function of Electrode Surface Area", *PACE*, vol. 14, pp. 1748–1751 (Nov. 1991).

*Primary Examiner*—William E. Kamm
*Assistant Examiner*—Scott M. Getzow
*Attorney, Agent, or Firm*—Fitch, Even, Tabin & Flannery

[57] ABSTRACT

The present invention provides an implantable electrical lead having relatively low electrical resistance. The lead comprises: a wire core formed in a helical coil having pre-compression, and having distal and proximal ends; a layer of an electrically conductive material formed around the wire core such that there is electrical continuity between the wire core and the metal layer; a biocompatible, electrically insulating sheath covering the wire core; a first lead connector electrically connected to the proximal end of the wire core; and an electrode electrically connected to the distal end of the wire core. The wire core may have various cross-sectional configurations which increase the current conducting area of the wire core without increasing its outside diameter. In another embodiment, the electrical lead includes a wire core having a cross-sectional area which differs over the length of the core to enhance the fatigue resistance of the electrical lead. In yet another embodiment, the wire core may be wound in a helix having different pitches in different sections of the core.

13 Claims, 3 Drawing Sheets

LOW RESISTANCE IMPLANTABLE ELECTRICAL LEADS

BACKGROUND OF THE INVENTION

The present invention relates to the field of electrical leads suitable for being implanted within living tissues, and more particularly to implantable electrical leads having relatively low electrical resistance which may be used in conjunction with cardiac pulse generators, neural stimulators, implantable sensors, and the like.

An implantable cardiac pulse generator, referred to generically as a cardiac pacer, or pacemaker, is a small, sealed electronic pulse generator that is used to treat irregular heart rhythms. In general, such pacers provide minute electrical stimuli to a heart when needed to speed up unnaturally slow heart rates.

An implantable cardiac defibrillator is a moderately sized, electronic pulse generator that is used to treat patients that are at risk from suffering lethal arrhythmias, most notably ventricular fibrillation. Ventricular fibrillation is a heart rhythm that typically results in death within several minutes. The defibrillator is used to provide large electrical stimuli when needed to interrupt the lethal arrhythmia and re-establish a life sustaining heart rhythm. Such pulse generators are typically packaged in sealed containers that are usually implanted subcutaneously in the thorax or abdomen of the heart patient. These devices monitor cardiac activity and deliver electrical pulses of appropriate intensity whenever needed. The energy supplied by a pulse generator is conducted along an electrically conductive cardiac lead from the pulse generator directly to the heart.

The pulse generator is commonly powered by a battery located inside the sealed container which is not intended to be replaceable. The amount of electrical energy stored in the battery generally determines the operational life of the pulse generator. Although the battery is very efficient at storing electrical energy, the battery life, and hence the operational life of the pulse generator, is usually less than ten years. The battery depletion is in part due to energy delivered to the heart, to energy consumed by the resistance of the electronic circuitry of the pulse generator and cardiac leads, and to self-discharge of the battery over time.

Each time an electrical pulse is delivered to the heart, some of the energy output of the battery is consumed by the cardiac leads as $I^2R$ heat, where "I" represents the current through the cardiac lead, and "R" represents the electrical resistance of the cardiac lead. The $I^2R$ losses represent wasted energy which provides no useful purpose. In an attempt to maximize the service life of the pulse generator, the lead materials and the geometries of the lead materials are chosen to minimize the electrical resistance of the cardiac leads while providing a lead that can withstand the rigors of exposure to repetitive stress.

The lead which electrically connects the pulse generator to the heart may be attached to the inner surface of the heart, the endocardium, or to the outer surface of the heart, the epicardium. Regardless of where the lead is attached to the heart, the lead is mechanically flexed with every heart beat. Every flexure of the lead creates stress within it. Since a typical heart rate is 60 beats per minute, the heart beats millions of times in a single year, and the lead is stressed with each beat.

Unlike a pulse generator, which is replaced when the battery is depleted, the lead is not normally replaced. A youthful patient who receives an implant may hopefully use the same lead or leads for decades. For this reason the materials comprising the lead should have excellent mechanical fatigue resistance.

Materials known as having low electrical resistance, such as copper or silver, are not well suited for use as a conductor in a cardiac lead because they cause tissue reactions and readily form oxides which may ultimately result in the fracture of a lead constructed with such material. A further disadvantage of copper and silver is that they have very poor resistance to repeated stress. Core copper wire, multi-stranded copper wire and even tinsel copper wire would poorly withstand the repeated, reversing stresses the heart would impose on cardiac leads comprised of copper wire. Leads of such constructions tend to fail after only a relatively small number of flexions, much as a paper clip breaks after being bent a few times.

Spring materials made of non-oxidizing, corrosion resistant alloys having good fatigue resistance perform much better mechanically as cardiac lead conductors than do conductors comprised of copper, silver, or their alloys. That is why for decades lead manufacturers have been using spring materials for the conductors in their leads. Examples of suitable conducting materials include stainless steel, such as Elgin Wire Co., Elgiloy, MP-35N, and titanium and titanium alloys.

Generally, in the construction of cardiac leads, the conducting wire core is coiled to form a tight helix composed of many individual coils, similar to an extension spring. The helical construction greatly lowers the mechanical stress to which the material comprising the wire core would otherwise be subjected by the beating heart. Though this construction provides long lasting leads, the electrical resistance of leads manufactured of spring steel or titanium is relatively high primarily due to the resistivity of the material comprising the wire core.

Low resistance leads are important both for pacing and defibrillation. DBS (drawn brazed strands) and DFT (drawn filled tubing) provide a cardiac lead having both reasonable fatigue resistance and electrical resistance. DBS and DFT are examples of two structures which combine low resistance, poor mechanical materials with the high resistance, spring materials of conventional leads. An example of DBS wire includes six strands of wire made of MP-35N that are brazed by a central silver core. An example of drawn filled tubing may include tubing fabricated of MP-35N and which is filled with silver. The silver, copper or other electrical conductor significantly reduces the lead resistance, but the silver or copper included in these leads also present several drawbacks. Chief among them are the toxicity and low fatigue life of copper and silver. There are several materials, as previously mentioned that are well suited to be pacing or defibrillation lead conductors. However, these materials unfortunately have high resistivities of about 100 micro-ohm-cm, as opposed to resistivities of about 1 micro-ohm-cm for copper or silver.

The electrical resistance of a typical cardiac lead is about 100 ohms. Cardiac leads with larger diameter conductors, high helix pitches (a measure of the number of coils per unit of axial length of the lead), multiple conductors, or smaller helical internal diameters, may have electrical resistances of about 10 ohms. However, such leads also tend to have reduced flex life.

A goal in the field of cardiac lead technology is to provide a cardiac lead having an electrical resistance of less than 1 ohm. Low resistance cardiac leads would provide a pulse generator with an increased service life because such leads would reduce $I^2R$ losses. Thus, more energy stored in the battery which powers the pulse generator would be able to be delivered to the heart because less energy would be wasted as heat. Therefore, it may be appreciated that there is a need for a cardiac lead having low electrical resistance, as well as good resistance to the repeated stresses to which a cardiac lead is exposed.

SUMMARY

The present invention provides an implantable electrical lead having relatively low electrical resistance and good mechanical resistance to cyclical stresses. The lead comprises a wire core formed into a helical coil having pre-compression, and having distal and proximal ends; a layer of an electrically conductive material formed around the wire core such that there is electrical continuity between the wire core and the electrically conductive layer; a biocompatible, electrically insulating sheath covering the helical coil; a first lead connector electrically connected to the proximal end of the wire core; and an electrode electrically connected to the distal end of the wire core. The term "biocompatible" refers to a material that is compatible with living tissue. Such material does not substantially react with the tissue nor cause inflammation or infection. Furthermore, biocompatible material is not rejected by living tissue.

The wire core may have an elongated cross-sectional area which is longer in the axial direction of the lead than in the radial direction. The elongated area provides a larger cross-sectional area having less resistance to electrical current flow per unit length through the core than would a wire core having a circular cross-sectional area with a diameter of the same length as the radial dimension of the elongated area.

In another embodiment of the invention, the electrical lead includes a wire core having a cross-sectional area which gradually tapers, or varies, over the length of the wire core from a small cross-sectional area to a larger cross-sectional area. One benefit of a such a varying cross-sectional area is that the section of the core having the smaller cross-sectional area is capable of withstanding the high repetitive loads from the beating heart while the section of the lead not subject to such loads has a larger cross-sectional area, and therefore, relatively less electrical resistance per unit length.

In yet another embodiment, the wire core may be wound in a helix having different pitches in different sections of the core. Sections of the lead having a high helix pitch are more resistant to repeated loads from the heart. Sections of the lead having a low helix pitch have less electrical resistance per unit length of the lead.

In a further embodiment, the electrical lead of the present invention includes a wire core wound into a helix having individual coils with pre-compression. The pre-compression assures that the coils contact one another at the interfaces between the coils. The two coils at every mth interface are welded together to promote axial current flow through those coil pairs, where m represents a positive integer. Such welding reduces the electrical resistance of the electrical lead.

BRIEF DESCRIPTION OF THE DRAWINGS

The above and other aspects, features, and advantages of the present invention will become more apparent from the following, more detailed description presented in conjunction with the following drawings wherein.

Throughout the specification and various views of the drawings, like components are referred to with like reference numerals.

DESCRIPTION OF THE PREFERRED EMBODIMENTS

The following description is of the best mode presently contemplated for carrying out the invention. This description is not to be taken in a limiting sense, but is made for the purpose of describing the general principles of the invention. The scope of the invention should be determined with reference to the claims.

Conventional cardiac pacing and defibrillation leads commonly employ corrosion resistant spring metal, such as spring steel, Elgiloy, MP-35N, titanium or titanium alloy, as a conducting material because such material has excellent resistance to metal fatigue. A wire core made of the conducting material is wound into a helix to form an electrical lead comprising a series of individual coils. The types of materials which commonly comprise the wire core generally exhibit thin metal oxide layers having high electrical resistance which impede the axial flow of current through the lead, thereby limiting the current to flow in a helical path through the cross-sectional area of the wire core. Although it is possible to remove the oxide, it is difficult to prevent the oxide from reforming in-vivo.

Figure 1:
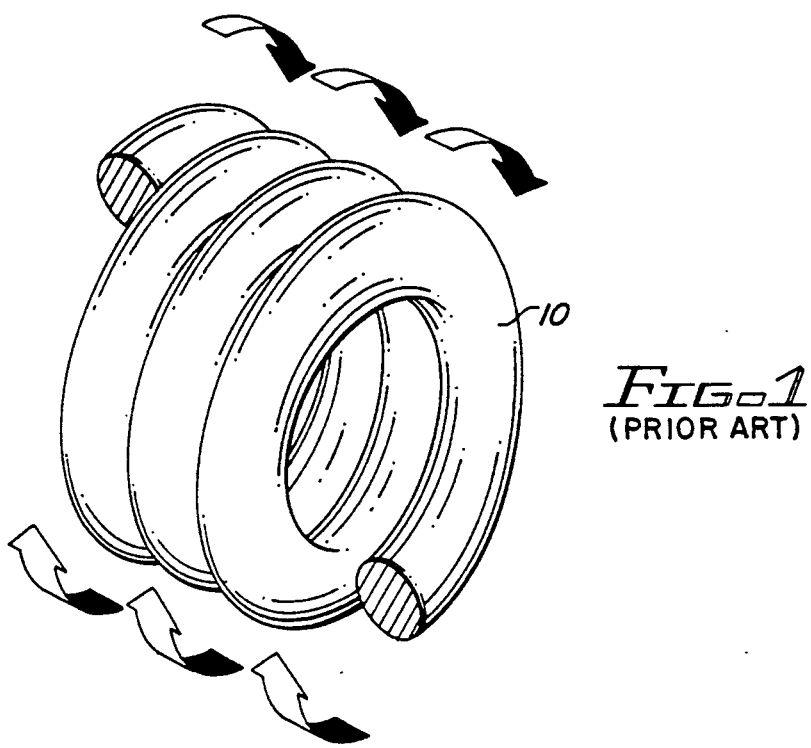
FIG. 1 shows a prior art wire core of an electrical lead which is wound in a helix.
Figure 2:
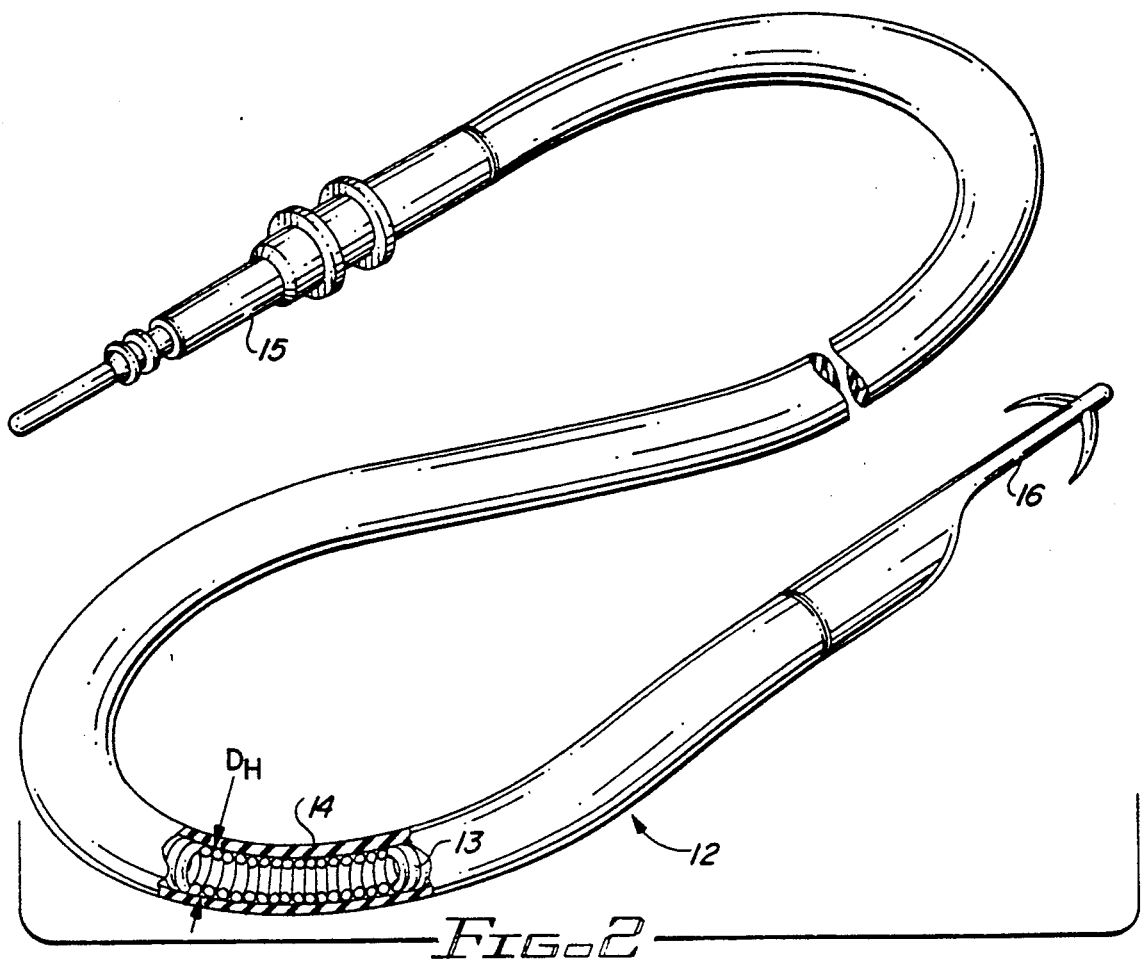
FIG. 2 illustrates the general configuration of an electrical lead embodying various features of the present invention.

The present invention provides an electrical lead having a much lower electrical resistance than do conventional leads, as well as good resistance to systematic stress. In general, an electrical lead 12 embodying various features of the present invention is shown in FIG. 2 to include a wire core 13 coated with an electrically insulating, biocompatible sheath 14. The wire core is wound into a helix having a helix diameter, $D_H$, which is to be distinguished from the diameter of the circular cross-section of the wire core. A lead connector 15 is electrically connected to the proximal end of the end of the wire core 13 and may, for example, be designed to connect the lead to the output connector of a pacemaker or defibrillator. By way of example, the lead connector 15 may be a VS-1 bipolar or unipolar pacemaker lead connector, as set forth in Calfree, R.V., and Saulson, S.H., "A Voluntary Standard For 3.2 MM Unipolar And Bipolar Pacemaker Leads And Connectors," *PACE*, Vol. 9, Part II, November-December 1986. An electrode 16 for electrically coupling the electrical lead to a heart is electrically connected to the distal end of the wire core 13. There are many types of electrodes which may be employed in conjunction with the present invention. Such electrodes may include ring electrodes, hemispherical tip electrodes, and such electrodes as are described in U.S. Pat. Nos. 3,974,834, 4,643,201, and 4,998,975, incorporated herein by reference.

Although the electrical lead of the present invention is generally described below with reference to applications involving cardiac pulse generators, it is to be understood that the electrical leads of the invention may also be used in other applications in which it is desirable to implant low resistance electrical leads within a living body, as for example, in that of a mammal, and more particularly, in a human. For example, electrical leads of the present invention may be used in conjunction with neural stimulators or sensors implanted within a living body.

Figure 3:
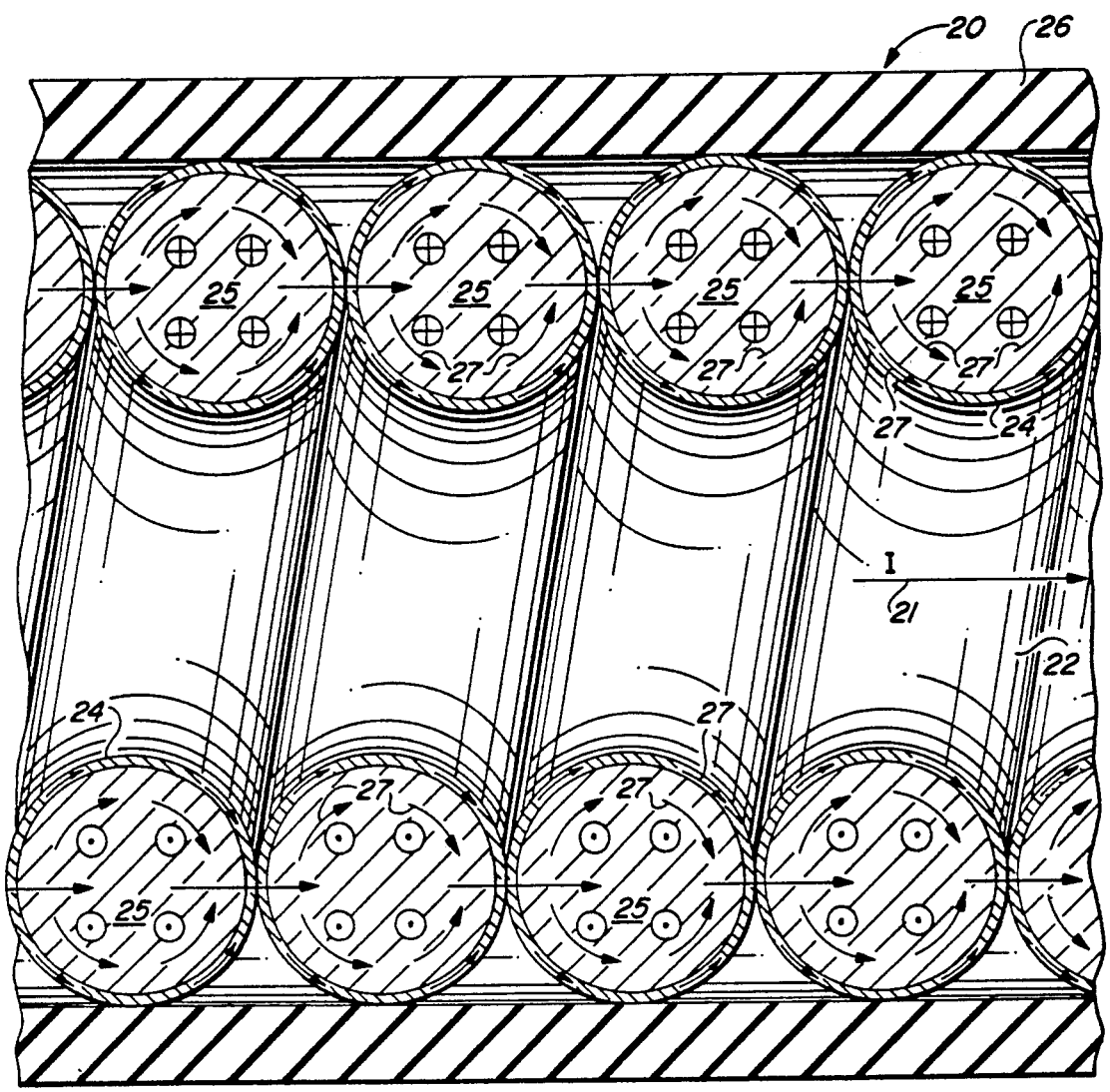
FIG. 3 is a cross-sectional view of an electrical lead having a wire core wound in a helix around which is formed an electrically conductive layer.

More specifically, a short length of an electrical lead 20 embodying various features of the present invention is shown in cross-section in FIG. 3. Referring now to FIG. 3, lead 20 is comprised of a wire core 22 wound in a helix and comprised of a material having good resistance to mechanical fatigue. By way of example, the wire core may be made from non-corrosive, bioresistant spring metal, such as spring steel, Elgiloy, MP-35N, titanium or titanium alloy, having a diameter which may be 0.1 mm and which may be coated with a biocompatible, electrically conductive layer 24 having a thickness of about 1 micron. The conductive layer may be composed of electrically conductive noble metals or their alloys, electrically conductive polymers, or carbon. The conductive layer 24 need only be sufficiently thick so as to not be abraded through to the underlying wire core 22 in response to any motion of the lead 20. An electrically insulating, tubular sheath 26 is placed over the helical coil formed of the coated, helically wound wire core 22 to electrically insulate the helical coil from surrounding tissues. The sheath 26 is preferably fabricated from a biocompatible, electrically insulating elastomeric material, such as polyurethane or silicone having a wall thickness of about 0.4 mm.

Assuming electrical current flow through the lead 20 is in the direction of the arrow 21, then axial current flow between successive coils 25 is represented by the arrows 27 shown in FIG. 3. Current also flows in a helical path through the wire core 22 such that the symbols "⊕" represent current flow in a direction into the FIG. 3, and the symbols " " represent helical current flow through the cross-sectional area of the wire core 22 in a direction coming out of FIG. 3. Current flows serially from one coil 25 to an adjacent coil 25 through the electrically conductive layer 24 surrounding the wire core 22. Current flow through the electrically conductive layer 24 is parallel to the current flowing in the helical path through the wire 22. Therefore, a thin layer of the electrically conductive layer 24 achieves a significant reduction in the electrical resistance of the lead 20. The conductive coating 24 should be composed of a material which remains conductive on its surface even after decades of being implanted within the body. Such conductive materials include the noble metals, conductive polymers, and conductive carbon. An example of a particularly suitable noble metal is platinum.

The electrical resistance of a material is directly related to the product of the intrinsic resistivity of the material multiplied by the length of the current path through the material, and is inversely related to the cross-sectional area of the material. The electrical lead 20 achieves the beneficial result of low electrical resistance by effectively reducing the length of the circuit path through the wire core 22. This result is achieved by allowing electrical current to flow from coil to coil, axially along the length of the lead, as well as in a helical path through the cross-sectional area of the wire core 22.

If local yielding or cracking of the electrically conductive layer 24 occurs at one location along the lead 20 with no effect on the underlying wire core 22, electrical current still conducts from coil to coil until a crack is encountered. Then, the electrical current simply conducts around such crack through the electrically conductive layer 24 and/or through the core material to the adjacent coil.

Platinum or platinum alloys are preferred materials for the electrically conductive layer 24 because they are excellent electrical conductors, have excellent immunity to oxidation, and are biocompatible. However, other metals such as gold or gold alloys may also be employed to comprise the conducting layer 24. If such metals are not biocompatible, then in addition to electrically insulating the wire core from the surrounding tissues, the sheath 26 also provides the important function of preventing contact between the electrically conductive layer 24 and the surrounding tissues, and/or bodily fluids.

In the case where the electrically conductive layer 24 is a metal, the metal layer may be formed on the wire core 22 by any of a number of well known manufacturing methods, e.g., sputtering, plating, condensation, etc. Generally, the electrically conductive layer 24, whether formed of metal, polymers, or carbon, should be formed on the wire core 22 before the wire core 22 is wound into a helical coil in order to ensure that the wire core is completely coated with the conductive layer. Alternatively, the electrically conductive layer 24 may be applied to the wire core 22 after the wire core 22 is wound into the helical coil while the coil is maintained elastically separated. After the electrically conductive layer 24 is applied, the coil is allowed to return to its compressed condition for use in the lead. Any electrically insulating oxides or films that may be present on the surface of the wire core 22 must be substantially removed before forming the electrically conductive layer 24 on the wire core 22 in order to provide good electrical continuity between the wire core and the electrically conductive layer 24. An example of one technique for removing such oxides or films from the surface of the wire core 22 involves etching the wire core with an acid in an inert atmosphere, such as argon or nitrogen, before forming the conductive material thereon. The removal of such films and oxides also promotes mechanical adhesion between the conductive layer 24 and the surface of the wire core 22.

In the preferred embodiment, the wire core 22 should be wound into a helix having pre-compression between the coils. Such pre-compression increases the contact area and provides good electrical contact between the individual coils 25 comprising the lead 20.

A conventional cardiac lead is constructed to have a uniform cross-sectional area over most of its length which can bear the cyclical stresses to which a portion of it is subjected. Despite the relatively long length of a typical cardiac lead, there are only a limited number of sections along the length of the lead which are subject to fatigue failure. One of these sections is that part of the lead in and near the heart itself. This section experiences millions of reversing stresses generated by the beating heart. Another section of the lead that experiences stress is near the pulse generator where the lead wraps around the implanted pulse generator. In the region of the pulse generator, however, skeletal motion causes the lead to flex much less frequently than the lead flexes near the heart.

The electrical resistance of the electrical lead 20 shown in FIG. 3 may be estimated in accordance with the following analysis. Assuming that an electrically conducting, biocompatible electrically conductive layer 24 has been formed on the wire core 22, the contact area between the individual coils comprising the helically wound wire core may be approximated using formulae empirically derived for materials in which the stress in an elastic body is proportional to the strain to which the body is subjected by an applied load (i.e., the material behaves in accordance with Hooke'law). Further assuming that the wire core 22 is wound into a helix with a pre-compression resulting from, say for example, a 0.001 inch coil overlay, the initial compression between individual coils is about 0.16 pounds, resulting in a region of contact about 0.016 micro-inches wide over a helix length of the wire core.

The total electrical resistance of an implantable electrical lead 20 as embodied by the present invention may be estimated by calculating the resistances of a single coil and of the contact area between adjacent coils, and then adding these resistances for each coil and contact area comprising the lead. For a lead coil made with 0.020 inch internal diameter winding of a 0.005 inch diameter MP-35N wire coated with about a 1 micron thick layer of platinum, and assuming that all current conducts to neighboring coils only through the contact regions, yields a predicted electrical resistance value of 4.2 ohms per axial meter of the lead. Much of the current will flow through the platinum, never entering the MP-35N, however, not all the current conducts from coil to coil. For a unifilar lead, less than 1% of the current is conducted in a helical path through the MP-35N cross-sectional area of the wire core in parallel with the axial flowing current. A portion of the current conducts through the platinum along the inside diameter of the helix which provides an electrical resistance contribution of about 6.6 ohms/m. Similarly, conduction along the outer surface of the helix provides an electrical resistance of about 8.8 ohms/m. These three parallel resistances combine to provide the lead 20 with an electrical resistance, R, where $$1/R = 1/4.2 + 1/6.6 + 1/8.8.$$

Therefore, an estimate of the total resistance, R, of the electrical lead 20 is about 2 ohms per meter. For a typical lead length, the total resistance is approximately 1 ohm.

Another embodiment of the present invention provides an electrical lead having reduced electrical resistance which is achieved by providing the wire core with a cross-sectional area which varies over the length of the lead. Such a lead may include a wire core having a tapered cross-sectional area to provide a large cross-sectional area in sections of the lead subject to low repetitive stresses, and a small cross-sectional area in sections of the lead subject to the severe repetitive stresses. The sections of the lead in which the wire core has the large cross-sectional area have relatively low electrical resistance per unit length through the helically wound wire core. However, these sections have limited flexibility making them less tolerant of repetitive, cyclical stress than the sections of the wire core having the smaller cross-sectional area. Therefore, a wire core can be configured with sections having cross-sectional areas well suited to the particular environment in which those sections are to be situated.

Figure 4:
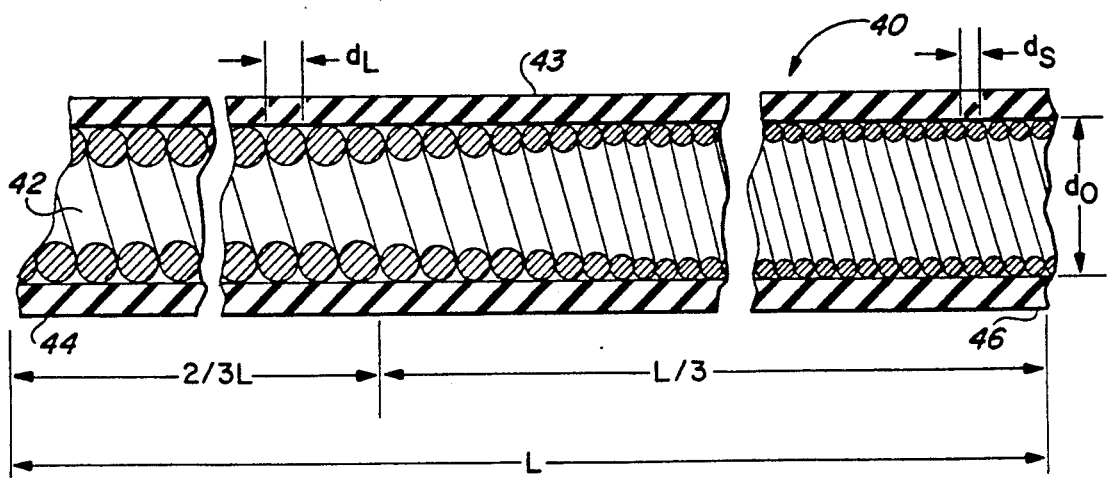
FIG. 4 is a cross-sectional view of an electrical lead having a wire core with a varying cross-sectional area.

Referring now to FIG. 4, an electrical lead 40 embodying various features of the present invention is shown to include a helically wound wire core 42 comprised of material having good mechanical fatigue resistance, such as MP-35N, coated with a biocompatible, electrically insulating elastomeric sheath 43. The sheath 43 may for example, be comprised of a 0.4 mm thick layer of pellethane. The wire core 42 maintains a uniformly round outside helix diameter, "$d_o$", over its entire length. However, the diameter, "$d_1$," of the wire core 42 itself over its length, providing the lead 40 with variable stiffness appropriate for the types of forces to which particular sections of the lead are subjected. The wire core 42 is designed to minimize mechanical stress in the sections where the lead 40 is subject to high repetitive mechanical loads, as for example, near the heart, and to minimize electrical resistance in all other sections of the lead. It should be noted that the taper of the wire core may be precisely controlled so as to be as gradual as desired. Generally, the more gradual the taper, the less stress concentration there is in the tapered section of the wire core.

The sections of the wire core 42 near the proximal end 44 of the lead 40 preferably have a relatively large cross-sectional area to minimize electrical resistance in that section of the lead. However, the large cross-sectional area of the wire core 42 in that section of the lead provides less resistance to mechanical fatigue than would a smaller diameter wire core. The proximal end 44 is commonly electrically connected to a lead connector, as for example, the lead connector 15 of FIG. 2. The wire core 42 at the distal end 46 of the lead 40 has a relatively small diameter, providing the wire core with good flexibility and resistance to mechanical fatigue in that section. However, disadvantageously, a small diameter wire has higher electrical resistance per unit length than would larger diameter wire of the same material. Therefore, the length of the section having the smaller cross-sectional area is made as short as possible in order to minimize the electrical resistance of the lead, yet long enough to provide the lead with sufficient resistance to withstand the stresses imposed in the lead by the beating heart. The distal end 46 of the lead 40 is generally connected to an electrode, such as the electrode 16 of FIG. 2.

The wire core 42 of FIG. 4 has a uniform outside diameter (isodiametric), $d_o$, and may be manufactured by winding a suitable wire around an appropriately tapered mandrel. As an alternative to having a isodiametric outside diameter, the wire core 42 may be wound so that it has a uniform inside helix diameter by winding the wire core 42 around an isodiametric mandrel, not shown.

The wire core 42 also may be coated with a suitable electrically conductive layer, as for example, an electrically conductive noble metal such as platinum or a platinum alloy, as described herein above, or with a layer of carbon or an electrically conductive polymer to further reduce the electrical resistance of the lead 40.

The proximal section of the lead is preferably sufficiently flexible so that the lead may be wound around the pulse generator implanted in the chest of the patient, as is common practice in the field of pacemaker implantation. However, the proximal end of the lead 40 is generally not flexed often during normal activities, nor is most of the length of the lead between the pulse generator and the heart frequently flexed and stressed. Generally, only the section of the wire core nearest the heart is highly and repeatedly flexed. Therefore, the lead 40 may be constructed, as shown by way of example in FIG. 4, whereby the wire core 42 has a relatively large diameter for the proximal ⅔ of the overall length, "L", of the lead and a smaller diameter for the distal ⅓ of the length of the lead. The larger diameter of the wire core 42 may be approximately 0.2 mm, and gradually tapers over a predetermined length to a smaller diameter of about 0.1 ram, although other diameters suitable for a particular application may also be employed.

A wire core having a varied diameter, as described above, may be manufactured, for example, by feeding a wire of uniform diameter through an etchant, such as an aqua regia, at varying speed. A length of wire having a smaller diameter may be manufactured by feeding the wire through the etchant at relatively slow speed so that the wire core is exposed to the etchant a sufficient time for the etchant to chemically etch the wire core to a predetermined diameter. The length of wire having the cross-sectional area which tapers from the smaller diameter to the larger diameter may be obtained by gradually increasing the speed of the wire through the etchant, thereby producing a wire core having a tapered diameter with no discontinuities.

Figure 5:
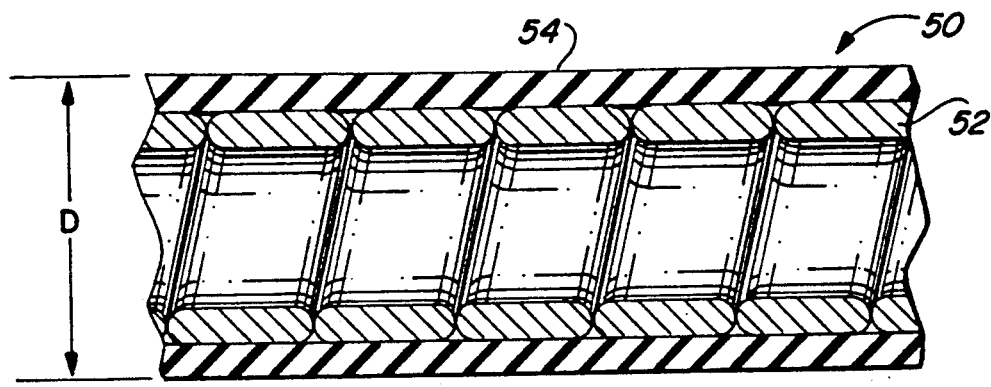
FIG. 5 shows a cross-sectional view of an electrical lead including a wire core having a cross-sectional area which is longer in the axial direction than in the radial direction.

An electrical lead having relatively low electrical resistance and embodying various features of the present invention may include a helically coiled wire core having a given helix outside diameter, and an elongated cross-sectional area. The axial dimension of such elongated cross-sectional area is greater in the axial direction along the length of the lead than in the transverse, or radial direction. For example, as shown in FIG. 5, an electrical lead 50 is shown to include a wire core 52, having, by way of example, an oval-shaped cross-sectional area where the dimension of the oval in the axial direction of the lead 50 is greater than the radial or transverse direction along the diameter, "D," of the helix. The lead is surrounded by a 0.4 mm thick insulating sheath 54 such as polyurethane or silicone. The benefit of the oval cross-sectional area is that it provides the electrical lead 50 with a greater cross-sectional area and shorter length through which the current flows helically than would an implantable electrical lead comprised of a wire core having a circular cross-sectional area and the same helix diameter, "D." The combination of both the increased cross-sectional area and reduced length serve to provide the lead with relatively low electrical resistance.

A wire core having an oval-shaped cross-sectional area may be manufactured by well known techniques such as extruding heated and softened material of which the wire is comprised through a suitably shaped die, or flattening a wire having a circular cross-sectional area with a roller mill. A wire core, such as wire core 52, may also be shaped to have other cross-sectional areas, such as rectangles or ellipses, oriented so that when the wire is coiled, the cross-sectional area of the wire core is longer in the axial direction than in the radial direction.

Figure 6:
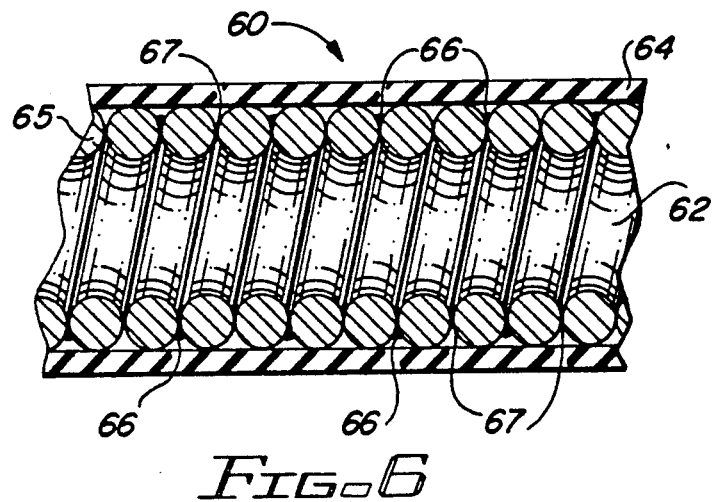
FIG. 6 show a cross-sectional view of an electrical lead including a wire core in which some of the individual coils are welded to one another.

In another embodiment of the present invention, an electrical lead 60, as shown in FIG. 6, having relatively low electrical resistance may include a helically wound wire core 62 comprised of individual coils 65 sheathed in a biocompatible electrical insulator sheath 64 which electrically isolates the wire core 62 from the surrounding tissues and bodily fluids. Adjacent coils 65 contact one another at interfaces 67 between coils. Every mth interface 67 between the coils 65 is welded so as to provide electrical continuity between the adjacent coils 65, where m is a positive integer, and the welds are represented by reference numbers 66. For example, every third interface 67 may be welded to the coils forming the interface along a weld line 66.

Figure 7:
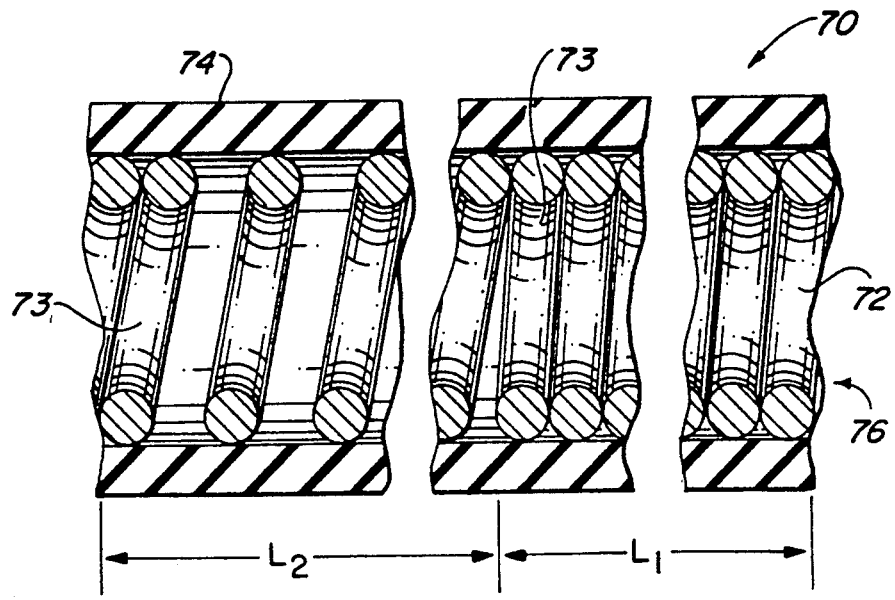
FIG. 7 is a cross-sectional view of an electrical lead having a wire core wound in a helix comprised of a series of coils in which the coils are wound with different helix pitches.

An electrical lead 70 embodying various features of the present invention, as shown in FIG. 7, and having relatively low electrical resistance may include a helically wound wire core 72 comprised of coils 73 sheathed in a biocompatible electrical insulator sheath 74. The wire core 72 is wound with a helix pitch which differs over the length of the lead. The length, $L_1$, of the electrical lead 70 is suitable for being positioned near the heart where it will be subjected to high, repetitive stresses. Therefore, the length $L_1$ is wound to have many closely spaced coils, i.e., a high helix pitch, whereas the length, $L_2$, of the electrical lead 70, not subjected to high stress levels may include coils wound with a lower helix pitch. The helix pitch may be defined as the number of coils of the wire core per unit length of the lead. The sections of the electrical lead having the coils 73 with the lower helix pitch provide the electrical lead 70 with a shorter, helical electrical path length for a given overall axial length of the lead than would a section of the lead where the coils have a higher helix pitch. Therefore, the section of the lead 70 having the lower helix pitch has less electrical resistance than does the section having the higher helix pitch.

The electrical lead shown in FIG. 7 has variable stiffness attributable to the varying helix pitch over the length of the wire core. Such variable stiffness may be used to promote forming the lead into desired shapes. For example, the relatively flexible section of length $L_1$ includes the distal end 76 of the lead 70. Such distal end 76 may be formed into an atrial "J," a common lead preform shape which maintains a stable lead position in the right atrial appendage of the heart. Such preform shape may also reduce the load that an electrode, not shown, mounted to the distal end of the lead exerts on the heart by reducing the inertial load of the lead against the heart.

It has been shown that the present invention provides several embodiments of electrical leads having very low electrical resistance and excellent fatigue resistance. An electrical lead having low electrical resistance is expected to increase the operational life of an implanted pulse generator by reducing the expenditure of energy stored in the pulse generator battery that is wasted in the form of $I^2R$ heating losses. Furthermore, such electrical leads may be manufactured from materials commonly employed in the construction of standard cardiac leads using well known manufacturing techniques.

It is to be appreciated that the present invention may be practiced utilizing other lead constructions than those described herein such as multifilar, i.e., multiple wire core, construction.

While the present invention has been described in terms of preferred embodiments, it is to be understood that the invention is not to be limited to the exact form of the apparatus or processes disclosed. Therefore, it is to be understood that the invention may be practiced other than as specifically described without departing from the scope of the claims.

What is claimed is:

1. An implantable electrical lead, comprising:
   an electrically conductive wire core formed into a helical coil having individual coils with precompression between said coils, having distal and proximal ends;
   a layer of an electrically conductive material formed around said wire core to provide electrical continuity between said wire core and said electrically conductive layer;
   a biocompatible, electrically insulating sheath covering said layer of electrically conductive material formed on said wire core; a first lead connector electrically connected to said proximal end of said wire core; and
   an electrode electrically connected to said distal end of said wire core.

2. The electrical lead of claim 1 wherein said electrically conductive layer includes a material selected from the group of noble metals.

3. The electrical lead of claim 2 wherein said wire core is made of spring metal.

4. The electrical lead of claim 1 wherein said material comprising said conductive layer is biocompatible.

5. The electrical lead of claim 1 wherein said conductive material includes carbon.

6. The electrical lead of claim 1 wherein said conductive material includes an electrically conductive polymer.

7. The electrical lead of claim 1 wherein the surface of said wire is substantially stripped of any materials having high electrical resistance before said electrically conductive layer is formed around said wire core.

8. The electrical lead of claim 1 wherein said wire core has a cross-sectional area which varies over the length of said wire core.

9. The electrical lead of claim 8 wherein said wire core includes a first predetermined length having a first cross-sectional area with a first diameter, a second predetermined length having a second cross-sectional area with a second diameter, and a third predetermined length between said first and second predetermined lengths in which said first diameter tapers to said second diameter.

10. The electrical lead of claim 1 wherein said wire core has an elliptical cross-sectional area.

11. The electrical lead of claim 1 wherein said wire core has a rectangular cross-sectional area.

12. The electrical lead of claim 1 wherein said wire core comprises a wire core formed in a helix including helical coils with pre-compression between said coils to form contact areas between adjacent of said coils, where every mth said contact area is welded to said adjacent coils, where m is a positive integer.

13. The electrical lead of claim 1 wherein said wire core has a first helix pitch over a predetermined length of said wire core and a second helix pitch over a second predetermined length of said wire core.

* * * * *